(12) United States Patent
Seddon

(10) Patent No.: US 12,121,418 B2
(45) Date of Patent: Oct. 22, 2024

(54) WOUND DRESSING CONSTRUCT WITH HIGH WICKING ADHESIVE BORDER

(71) Applicant: Solventum Intellectual Properties Company, Maplewood, MN (US)

(72) Inventor: James Killingworth Seddon, Wimborne (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 289 days.

(21) Appl. No.: 17/637,767

(22) PCT Filed: Sep. 22, 2020

(86) PCT No.: PCT/IB2020/058836
§ 371 (c)(1),
(2) Date: Feb. 23, 2022

(87) PCT Pub. No.: WO2021/059124
PCT Pub. Date: Apr. 1, 2021

(65) Prior Publication Data
US 2022/0313493 A1    Oct. 6, 2022

(51) Int. Cl.
*A61F 13/00* (2024.01)
*A61F 13/0203* (2024.01)
*A61F 13/0246* (2024.01)

(52) U.S. Cl.
CPC ........ *A61F 13/022* (2013.01); *A61F 13/0223* (2013.01); *A61F 13/0246* (2013.01)

(58) Field of Classification Search
None
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

CA 2983906 C translation (Year: 2023).*
(Continued)

*Primary Examiner* — Kim M Lewis

(57) ABSTRACT

A wound dressing includes a patient interface layer, a wicking layer, an absorbent layer, and a cover layer. The patient interface layer is configured to engage a wound bed and has a first side and a second side, the second side configured to face the wound bed. The wicking layer, absorbent layer, and cover layer all also have a first side and a second side. A perimeter of the first side of the wicking layer is adhered to the second side of the cover layer, forming an adhesive border surrounding the wicking layer and the absorbent layer, and the wicking layer is configured to peripherally wick perspiration from underneath the adhesive border towards the center of the wicking layer and upwards towards the absorbent layer.

16 Claims, 6 Drawing Sheets

(56) References Cited

U.S. PATENT DOCUMENTS

| | | |
|---|---|---|
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 9,913,757 B2 | 3/2018 | Vitaris |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0003030 A1 | 2/2004 | Hunt et al. |
| 2004/0030304 A1* | 2/2004 | Hunt ............... A61L 15/425 |
| | | 604/317 |
| 2014/0163491 A1 | 6/2014 | Schuessler et al. |
| 2015/0080788 A1 | 3/2015 | Blott et al. |
| 2015/0245950 A1 | 9/2015 | Locke et al. |
| 2018/0214313 A1* | 8/2018 | Pratt ............... A61F 13/01029 |
| 2018/0214315 A1 | 8/2018 | Pratt et al. |
| 2020/0129341 A1* | 4/2020 | Coulthard ............ A61F 13/05 |

FOREIGN PATENT DOCUMENTS

| | | | |
|---|---|---|---|
| AU | 755496 B2 | 12/2002 | |
| CA | 2005436 A1 | 6/1990 | |
| CA | 2983906 C * | 11/2023 | ............ A61F 13/00 |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 2195255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |

(56) References Cited

FOREIGN PATENT DOCUMENTS

| WO | 94/20041 A1 | 9/1994 |
|---|---|---|
| WO | 96/05873 A1 | 2/1996 |
| WO | 97/18007 A1 | 5/1997 |
| WO | 99/13793 A1 | 3/1999 |

OTHER PUBLICATIONS

International Search Report and Written Opinion for Corresponding Application No. PCT/IB2020/058836 mailed Jan. 12, 2021.
Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Dukic, Ž. Maksimovic, D. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

WOUND DRESSING CONSTRUCT WITH HIGH WICKING ADHESIVE BORDER

CROSS-REFERENCE TO RELATED APPLICATIONS

This application claims the benefit of priority to U.S. Provisional Application No. 62/904,849, filed on Sep. 24, 2019, which is incorporated herein by reference in its entirety.

BACKGROUND

The present disclosure relates generally to a wound dressing. The present disclosure relates more particularly to a wound dressing having a patient interface layer, a wicking layer, and an absorbent layer, wherein the wicking layer is configured to wick wound exudate away from the patient interface layer and towards the absorbent layer. The present disclosure also relates to a wound dressing having an adhesive border surrounding the absorbent layer configured to prevent fluid leakage from the wound dressing.

It is often desirable to remove wound exudate from a wound bed to promote the healing of the wound. Wound dressings can be challenging to adhere to wound sites due to the amount of wound exudate and perspiration coming from the wound bed. In some cases, wound dressings include a layer of foam or other absorbent layer configured to absorb the wound exudate from the wound bed for these reasons. However, the absorption capacity of the wound dressings is such that not all of the wound fluid may be absorbed into the wound dressing. Additionally, perspiration from the skin surrounding the wound bed can cause wound dressings to prematurely lift from the skin.

It is often desirable to construct wound dressings with materials having high moisture vapor transmission rates (MVTR) in order to alleviate the problems associated with perspiration and wound exudate management. It would be desirable to provide a wound dressing that incorporates high MVTR capabilities while also providing an alternative method for managing perspiration and wound exudate that has accumulated underneath an adhesive dressing border.

SUMMARY

One implementation of the present disclosure is a wound dressing including a patient interface layer, a wicking layer, an absorbent layer, and a cover layer. The patient interface layer is configured to engage a wound bed, and has a first side and a second side, the second side configured to face the wound bed. The wicking layer has a first side and a second side, the second side configured to face the first side of the patient interface layer. The absorbent layer has a first side and a second side, the second side configured to face the first side of the wicking layer. The cover layer has a first side and a second side, the second side configured to face the first side of the absorbent layer. A perimeter of the first side of the wicking layer is adhered to the second side of the cover layer, forming an adhesive border surrounding the wicking layer and the absorbent layer, and the wicking layer is configured to peripherally wick perspiration from underneath the adhesive border towards the center of the wicking layer and upwards towards the absorbent layer.

Another implementation of the present disclosure is a method of making a wound dressing. The method includes providing a patient interface layer configured to engage a wound bed, and having a first side and a second side, the second side configured to face the wound bed. The method further includes placing a wicking layer, having a first side and a second side, atop the patient interface layer. The method further includes placing an absorbent layer, having a first side and a second side, atop the wicking layer. The method finally includes adhering a cover layer, having a high moisture vapor transmission rate, to an outer perimeter of the patient interface layer and the wicking layer, such that the cover layer is atop the absorbent layer, forming an adhesive border surrounding the absorbent layer. The wicking layer is configured to peripherally wick perspiration from underneath the adhesive border towards the center of the wicking layer and upwards towards the absorbent layer.

Another implementation of the present disclosure is a wound dressing including a patient interface layer, a wicking layer, an absorbent layer, and a cover layer. The patient interface layer has a plurality of fenestrations or perforations, a wound region configured to cover a wound bed, and a border region configured to overlie a periwound region surrounding the wound bed. The wicking layer lies atop the patient interface layer and is substantially coextensive with the patient interface layer. The absorbent layer lies atop the wicking layer, has a perimeter that is inset from, and non-coextensive with, the border region of the patient interface layer, is configured to draw perspiration from the periwound region up through the fenestrations or perforations in the border region and laterally through the wicking layer to the absorbent layer, and to draw wound exudate up through the fenestrations or perforations in the wound region and directly up through the wicking layer to the absorbent layer. Finally, the cover layer lies atop the absorbent layer and has an underside with an adhesive provided at least partially thereon that bonds with at least one of the wicking layer and the patient interface layer.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Figure 1:
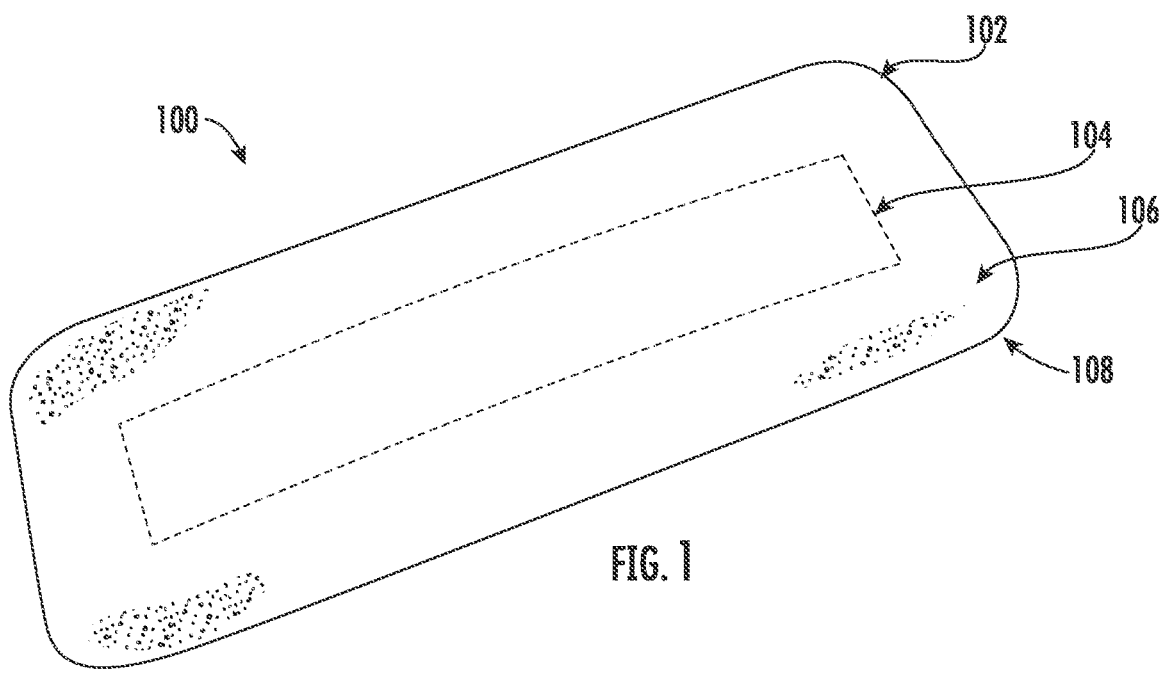
FIG. 1 is a top view of a wound dressing, according to an exemplary embodiment.

Referring generally to FIGS. 1-8, a wound dressing is shown, according to exemplary embodiments. The wound dressing of the exemplary embodiments has multiple layers including a patient interface layer, a wicking layer, an absorbent layer, and a cover layer. In some embodiments, the cover layer may be adhered around a perimeter to the patient interface layer, creating an adhesive border that surrounds the wicking layer and the absorbent layer. In some embodiments, the wicking layer is configured to wick perspiration from skin surrounding the wound bed and laterally transfer the perspiration into the absorbent layer. In some embodiments, the patient interface layer has a plurality of perforations or fenestrations in order to increase fluid uptake of the wound dressing, such that the wicking layer wicks fluid from the wound bed and through the perforations/fenestrations in the patient interface layer. In some embodiments, the patient interface layer may be provided in the form of adhesive border, such that the wicking layer adheres to the patient interface layer around its perimeter, and the wicking layer is in contact with the wound bed through the center opening of the patient interface layer. In still other embodiments, other configurations and layers of the wound dressing are possible.

Advantageously, the wicking layer helps in managing perspiration from the skin surrounding the wound bed. Excess perspiration from surrounding skin can cause wound dressings to lift from the application site. The wicking layer manages perspiration from the surrounding skin by laterally wicking the perspiration through the wicking layer and towards the absorbent layer. Moisture which may accumulate underneath the adhesive border is wicked through the wicking layer towards the absorbent layer in order to prevent lifting of the wound dressing from the skin. The wicking layer also increases the amount of wound exudate that is wicked away from the patient interface layer or from the wound bed itself and transferred towards the absorbent layer. In some embodiments, the patient interface layer has a plurality of perforations such that the wicking layer can easily wick fluid through the perforations in the patient interface layer. In other embodiments, the wicking layer is in direct contact with the wound bed. Additionally, the wicking layer wicks wound exudate towards the cover layer, such that it may be evaporated through the cover layer.

Another advantage provided by the wound dressing of the present disclosure is the incorporation of an adhesive border surrounding the absorbent layer, which is intended to prevent leakage of wound exudate and other fluids from the absorbent layer and back into the wound bed. In some embodiments, the cover layer adheres, on its perimeter, to the wicking layer and/or the patient interface layer, which creates the adhesive border surrounding the absorbent layer. The adhesive border helps retain absorption of the wound exudate within the absorbent layer, such that the wound dressing does not release any fluid back into the wound bed. The inclusion of the wicking layer aids in drawing moisture from underneath the adhesive border laterally through the wicking layer and towards the absorbent layer, where it can then evaporate into the atmosphere through the cover layer. Additional features and advantages of the wound dressing are described in detail below.

Wound Dressing

Figure 2:
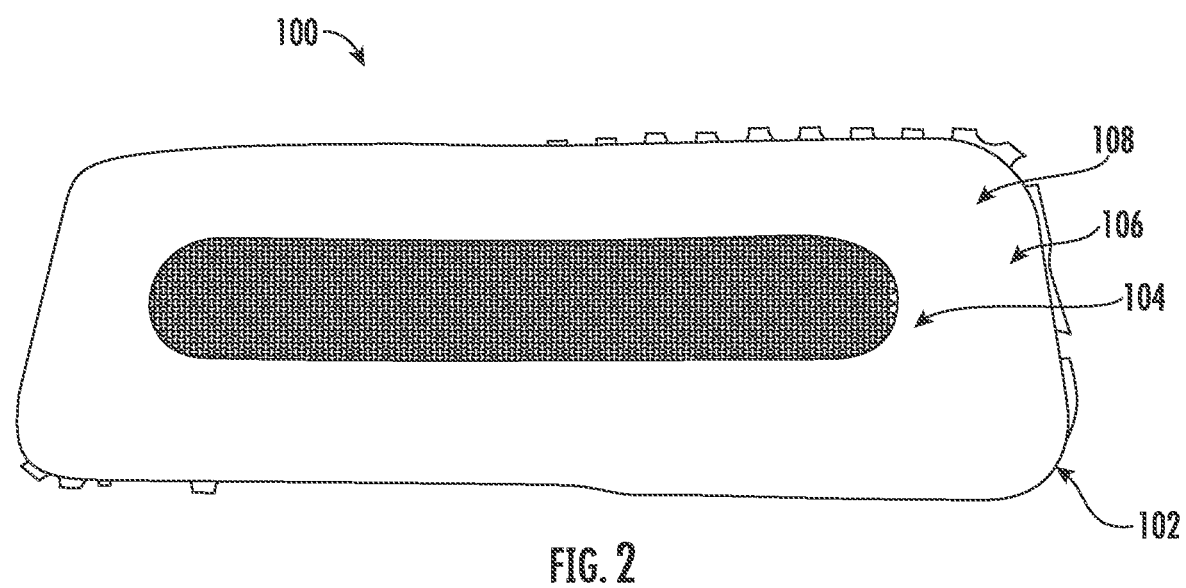
FIG. 2 is a bottom view of the wound dressing of FIG. 1, according to an exemplary embodiment.
Figure 3:
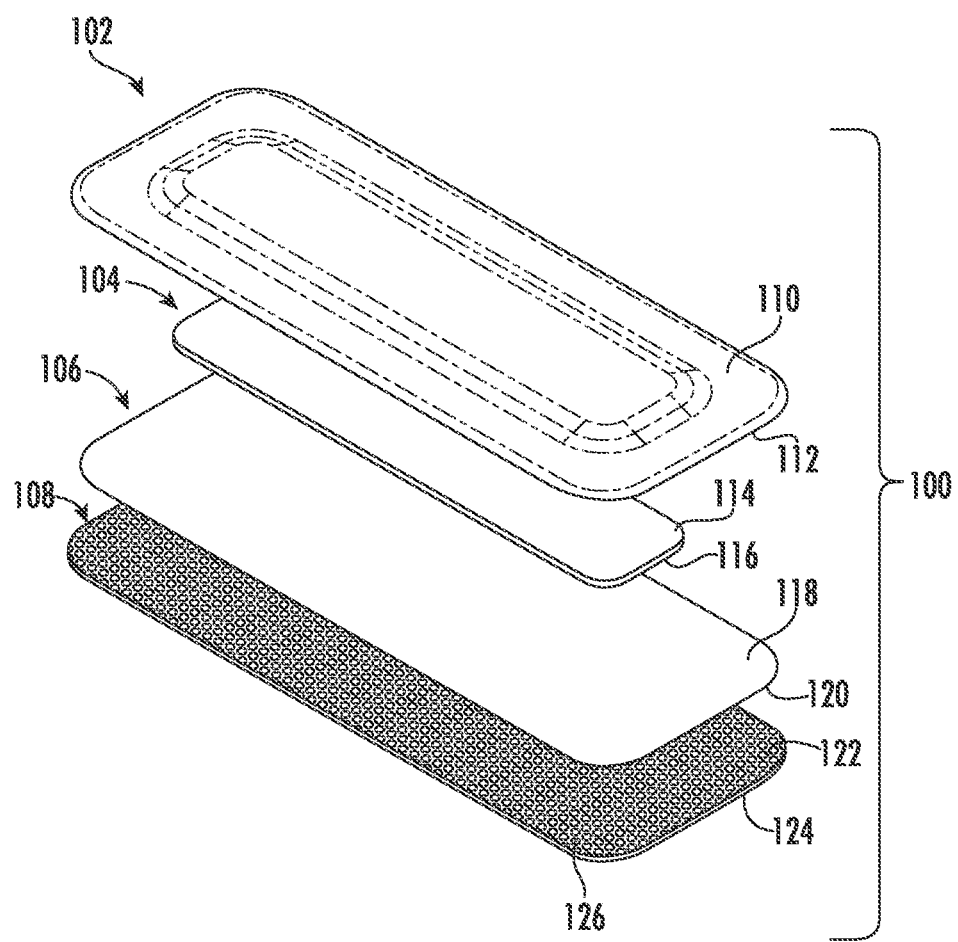
FIG. 3 is an exploded view illustrating several layers of the wound dressing of FIGS. 1 and 2, according to an exemplary embodiment.
Figure 4:
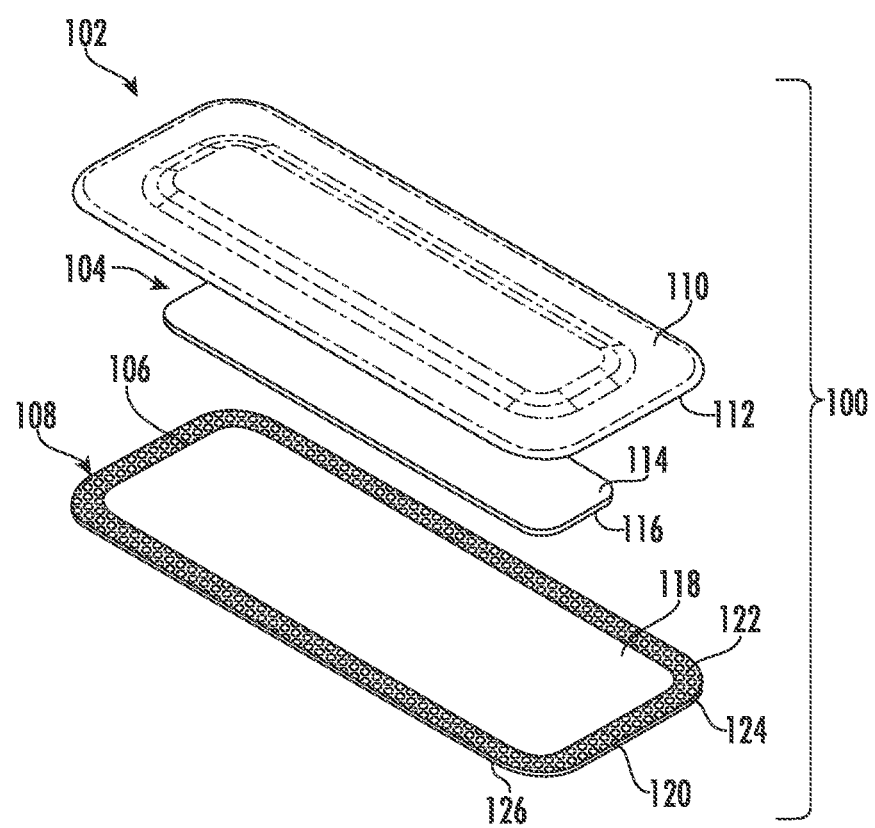
FIG. 4 is an exploded view illustrating several layers of the wound dressing of FIGS. 1 and 2, according to another exemplary embodiment.
Figure 5:
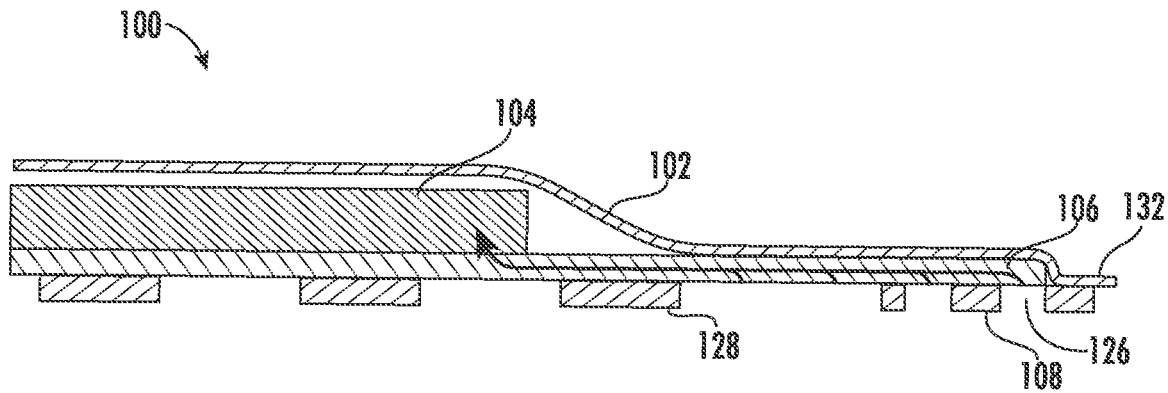
FIG. 5 is a cross-sectional view illustrating one side of the wound dressing of FIGS. 1 and 2, according to an exemplary embodiment.
Figure 6:
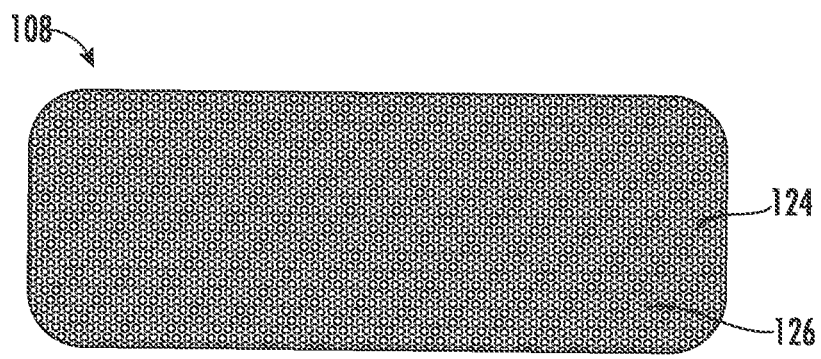
FIG. 6 is a bottom perspective view of a patient interface layer of the wound dressing of FIGS. 1 and 2, according to an exemplary embodiment.
Figure 7:
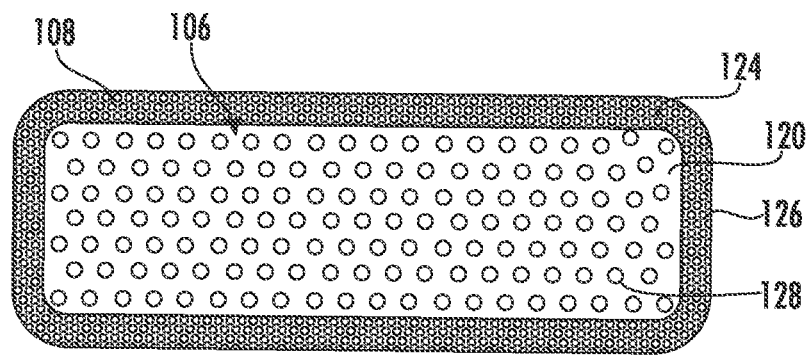
FIG. 7 is a bottom perspective view of the patient interface layer of the wound dressing of FIGS. 1 and 2, according to another exemplary embodiment.
Figure 8:
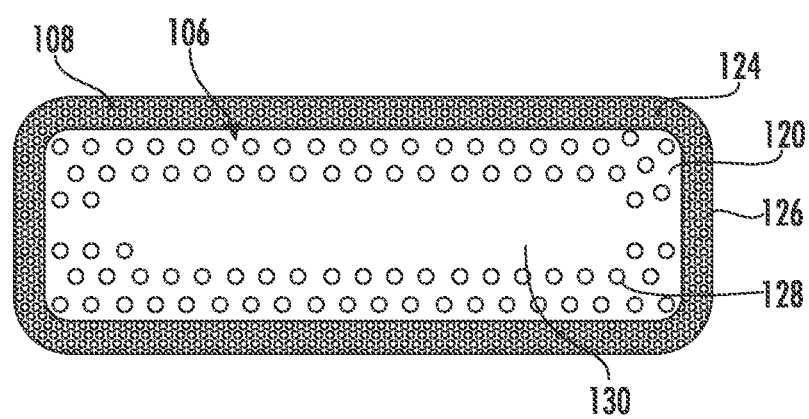
FIG. 8 is a bottom perspective view of the patient interface layer of the wound dressing of FIGS. 1 and 2, according to another exemplary embodiment.

Referring now to FIGS. 1-8, a wound dressing 100 is shown, according to an exemplary embodiment. In a brief overview, FIG. 1 is a top view of a wound dressing 100 as would be visible when wound dressing 100 is adhered to a surface (e.g., a patient's skin). FIG. 2 is a bottom view of wound dressing 100 showing the surface of wound dressing 100 configured to contact a wound. FIGS. 3-4 are exploded views of several exemplary embodiments illustrating components and layers 102-108 of wound dressing 100. FIG. 5 is a cross-sectional view of an exemplary embodiment illustrating one side of the wound dressing 100 close-up. FIGS. 6-8 are bottom views illustrating several exemplary embodiments of a patient interface layer of the wound dressing 100.

In various embodiments, wound dressing 100 can be formed as a substantially flat sheet for topical application to wounds, or formed as a contoured dressing for application to body surfaces having high curvature. The size and shape of wound dressing 100 can vary depending on the size of the wound to be dressed and its location. For example, it is contemplated that the size of wound dressing 100 can range from approximately 1 $cm^2$ to 200 $cm^2$, and more preferably from approximately 4 $cm^2$ to 100 $cm^2$. However, other shapes and sizes of wound dressing 100 are also possible depending on the intended use. In other embodiments, wound dressing 100 may have a substantially convex or concave shape, or other customizable topography to adhere to wounds located on areas such as the knee or elbow.

Wound dressing 100 is shown to include (among other possible layers) a cover layer 102, an absorbent layer 104, a wicking layer 106, and a patient interface layer 108. In some embodiments, the cover layer 102 adheres to one or more of the wicking layer 106 and the patient interface layer 108 (e.g., using an adhesive). In some embodiments, the wicking layer 106 may further be adhered to the patient interface layer 108. The cover layer 102 may comprise an adhesive border with an opening, such that cover layer 102 adheres to the perimeter of the patient interface layer 108 and the wicking layer 106 is exposed to the wound bed through the opening. In some embodiments, cover layer 102, wicking layer 106, and patient interface layer 108 may lie entirely in the confines of a periwound at the wound bed. In other embodiments, the cover layer 102 may extend past a perimeter of patient interface layer 108 and adhere to a top of the periwound. However, other configurations and locations of the layers are also possible depending on the intended use.

Cover Layer

In some embodiments, wound dressing 100 includes a cover layer 102. Cover layer 102 is shown to include a first side 110 and a second side 112 opposite first side 110. Second side 112 is configured to face a wound. When wound dressing 100 is applied to a wound, first side 110 faces away from the wound whereas second side 112 faces toward the wound. Cover layer 102 attaches over absorbent layer 104, wicking layer 106, and patient interface layer 108. In some embodiments, cover layer 102 is laminated to one or more of wicking layer 106 and patient interface layer 108 around only a perimeter of the second side 112 of cover layer 102, such that cover layer 102 is not adhered to the smaller absorbent layer 104. Cover layer 102 may be laminated to wicking layer 106 and/or patient interface layer 108 using a fusible fiber positioned between cover layer 102 and wicking layer 106. Cover layer 102 can be bonded to wicking layer 106 and patient interface layer 108, for example, by an adhesive or by radiation cross-linking. In some embodiments, cover layer 102 is bonded to the layers 106-108 by urethane or urea linkages. This can be achieved by applying cover layer 102 to layers 106-108 (substantially without mixing) before polyurethane curing is complete. In some embodiments, the adhesive applied to cover layer 102 is moisture vapor transmitting and/or patterned to allow passage of water vapor therethrough. The adhesive may include a continuous moisture vapor transmitting, pressure-sensitive adhesive layer of the type conventionally used for island-type wound dressings (e.g., a polyurethane or polyethylene-based pressure sensitive adhesive). One example of an adhesive which can be used is a pressure sensitive adhesive based on acrylate ester copolymers, polyvinyl ethyl ether and polyurethane, as described in Great Britain Patent Application No. 1280631A. The basis weight of the adhesive may be 20 to 250 g/m², and more preferably 50 to 150 g/m². In some embodiments, after the adhesive has been applied, a surface head (i.e., an iron) is applied to cover layer 102 such that cover layer 102 bonds to the layers 106-108.

In some embodiments, the entire second side 112 of cover layer 112 may be coated with an adhesive, either in a continuous coat or as a pattern coated adhesive. In other embodiments, the second side 112 of cover layer 102 may be coated with an adhesive solely on the perimeter of the second side 112, such that a central portion of second side 112 is free of adhesive. The adhesive-coated perimeter of second side 112 may provide a sealed border or a bond between the cover layer 102 and one or more of the wicking layer 106 and the patient interface layer 108 in order to prevent egress and ingress of the wound dressing 100. Thus, the absorbent layer 104 is surrounded by the adhesive border, providing a barrier which prevents fluid from leaking from the absorbent layer. In some embodiments, cover layer 102 may comprise both an adhesive cover layer and a non-adhesive cover layer. The adhesive cover layer may be applied over the non-adhesive cover layer and adhered to one or more of the wicking layer 106 and the patient interface layer 108. In some embodiments, the adhesive cover layer may be substantially ring-shaped or "picture frame" shaped, such that there is a central opening. Thus, when adhesive cover layer is placed over non-adhesive cover layer, a central portion of the non-adhesive cover layer remains exposed. Still other configurations and layers of the cover layer 102 are also possible.

In some embodiments, cover layer 102 is a thin layer of polyurethane film. One example of a suitable material for cover layer 102 is the polyurethane film known as ESTANE 5714F. Other suitable polymers for forming cover layer 102 include poly alkoxylalkyl acrylates and methacrylates, such as those described in Great Britain Patent Application No. 1280631A filed Nov. 22, 2002, the entire disclosure of which is incorporated by reference herein. In some embodiments, cover layer 102 includes a continuous layer of a high-density blocked polyurethane foam that is predominantly closed-cell. Cover layer 102 may have a thickness in the range of 10 μm to 100 μm, preferably in the range of 50 μm to 70 μm. In some embodiments, cover layer 102 has a thickness of approximately 60 μm. Cover layer 102 may be substantially permeable to liquid and moisture vapor. In other words, cover layer 102 may be permeable to both water vapor and liquid water such as wound exudate. Such permeability is intended to facilitate or enhance a hydrophilic gradient from the wound bed, through the wound dressing 100, and to the surrounding atmosphere. In some embodiments, cover layer 102 is impermeable to bacteria and other microorganisms. In other embodiments, cover layer 102 is configured to wick moisture from absorbent layer 104 and wicking layer 106 to first side 110 of cover layer 102, such that it may evaporate into the atmosphere. In some embodiments, cover layer 102 may be substantially hydrophilic and have a high MVTR, such as to permit evaporation of wound exudate/fluid from first side 110.

In the embodiments shown, the perimeter of cover layer 102 is even with the perimeter of patient interface layer 108. In other embodiments, the perimeter of cover layer 102 may extend beyond (e.g., circumscribe) the perimeter of patient interface layer 108 to provide a margin for wound dressing 100 (e.g., as an "island" dressing) to the skin of a patient adjacent to the wound being treated, and may comprise an adhesive on the second side 110 configured to attached to the wound.

Absorbent Layer

In some embodiments, wound dressing 100 includes an absorbent layer 104. Absorbent layer 104 is shown to include a first side 114 and a second side 116 opposite the first side 114. When wound dressing 100 is applied to a wound, first side 114 faces away from the wound whereas second side 116 faces towards the wound. In some embodiments, first side 114 of absorbent layer 104 contacts second side 112 of cover layer 102 while second side 116 of absorbent layer 104 contacts first side 118 of wicking layer 106. In some embodiments, absorbent layer 104 is configured to wick moisture from wicking layer 106 and distribute the moisture across first side 114. Absorbent layer 104 draws perspiration from the periwound region up through the perforations 126 in the border region of the patient interface layer 108 and laterally through the wicking layer 106 to the absorbent layer 104. Absorbent layer 104 also draws wound exudate from the wound bed up through the perforations 126 in the wound region of patient interface layer 108 and directly up through the wicking layer 106 towards the absorbent layer 104. In some embodiments, absorbent layer 104 is encapsulated between cover layer 102 and wicking layer 106 in a "loose" or free-floating manner. Absorbent layer 104 is smaller in dimension than either of the cover layer 102 and the wicking layer 106 such that the perimeter of cover layer 102 and wicking layer 106 both extend beyond the perimeter of absorbent layer 104. First side 114 of absorbent layer 104 is not adhered to second side 112 of cover layer 102. Similarly, second side 116 of absorbent layer 104 is not adhered to first side 118 of wicking layer 106. Absorbent layer 104 is substantially free-floating between cover layer 102 and wicking layer 106.

In some embodiments, absorbent layer 104 may comprise a superabsorbent polymer material. The superabsorbent polymer may include Luquasorb 1160 or 1161, such as may be commercially available from BASF. The superabsorbent polymer may be in the form of granules that are contained in a water soluble carrier polymer. One example of the water soluble carrier polymer is polyvinylpyrrolidone (PVP). In some embodiments, absorbent layer 104 may be in the form of a superabsorbent particulate or powder material. The particulate may be placed centrally between cover layer 102 and wicking layer 106, such that the particulate is encapsulated within cover layer 102 and wicking layer 106. Absorbent layer 104 may have a granular composition, such that the particulate is not held together by entanglement, weaving/knot, or lamination. Absorbent layer 104 in the form of a particulate or powder increases the flexibility of absorbent layer 104, which may act to reduce the overall rigidity of wound dressing 100. In some embodiments, absorbent layer 104 includes a flexible plasticized hydrophilic polymer matrix having a substantially continuous. Several examples of hydrophilic foams which can be used to make absorbent layer 104 are described in detail in U.S. Pat. No. 8,097,272 issued Jan. 17, 2012, U.S. Pat. No. 8,664,464 issued Mar. 4, 2014, and U.S. Pat. No. 8,058,499 issued Nov. 15, 2011. The entire disclosure of each of these patents is incorporated by reference herein. In other embodiments, absorbent layer 104 may be formed from aromatic or aliphatic precursors. Advantageously, absorbent layer 104 may provide enhanced absorbency for liquid exudate. This is because the porous structure of the foam provides for rapid uptake of liquid exudate. In some embodiments, absorbent layer 104 may allow for the evaporation of liquid exudate through the high MVTR cover layer 102.

In the embodiments shown, the perimeters of the cover layer 102, wicking layer 106, and patient interface layer 108 extend beyond the perimeters of absorbent layer 104, such that absorbent layer 104 is substantially smaller than the rest of the layers. In some embodiments, the perimeter of absorbent layer 104 is inset from, e.g., non-coextensive with, the border region of the patient interface layer 108, such that the absorbent layer 104 lies substantially atop the wound region of patient interface layer 108. In some embodiments, when cover layer 102 is adhered to wicking layer 106 and/or patient interface layer 108, absorbent layer 104 is surrounded by an adhesive border. Absorbent layer 104 is thus "free-floating" between cover layer 102 and wicking layer 106. Absorbent layer 104 is configured to retain wound exudate and other fluids that have been absorbed from the wound bed and to prevent any fluids from leaking from wound dressing 100.

Wicking Layer

In some embodiments, wound dressing 100 includes a wicking layer 106. Wicking layer 106 is shown to include a first side 118 and a second side 120 opposite first side 118. Second side 120 is configured to face a wound. When wound dressing 100 is applied to a wound, first side 118 faces away from the wound towards second side 116 of absorbent layer 104 and second side 120 faces towards the wound and towards a first side 122 of patient interface layer 108. Wicking layer 106 attaches over and lies atop the patient interface layer 108. In some embodiments, wicking layer 106 is configured to wick wound exudate from patient interface layer 108 towards absorbent layer 104 in order to increase fluid uptake within wound dressing 100. Wicking layer 106 aids in transferring fluid into absorbent layer 104 in order to manage perspiration within wound dressing 100. In some embodiments, wicking layer 106 comprises a high wicking material, such as Milliken Interdry or Libeltex TDL2. In other embodiments, other configurations and materials for wicking layer 106 are possible.

In some embodiments, a perimeter of first side 118 of wicking layer 106 may be laminated or otherwise adhered to the second side 112 of cover layer 102. The adhesion of cover layer 102 to wicking layer 106 provides an adhesive border surrounding absorbent layer 104, which helps to prevent the release of wound exudate and other fluids from absorbent layer 104. In some embodiments, a central portion of first side 118 is not adhered to second side 116 of absorbent layer 104, such that absorbent layer 104 remains free-floating within wound dressing 100. In the embodiments shown, cover layer 102 and patient interface layer 108 extend beyond the perimeter of wicking layer 106 by a distance 132 of 2 mm to 10 mm. In other embodiments, the perimeter of wicking layer 106 may be even with the perimeter of the cover layer 102 and/or the patient interface layer 108. In some embodiments, wicking layer 106 is substantially coextensive with patient interface layer 108, such that the perimeters of wicking layer 106 and patient interface layer 108 are even.

In some embodiments, wicking layer 106 is laminated or adhered to patient interface layer 108. In some embodiments, second side 120 of wicking layer 106 comprises a plurality of adhesive deposits 128, as seen in FIGS. 5 and 7-8, configured to adhere wicking layer 106 to patient interface layer 108. The adhesive deposits 128 may be acrylic adhesive or any other suitable type of adhesive. In the embodiment shown in FIGS. 4-5 and 7-8, wicking layer 106 is exposed to the wound bed or other application site through a central opening within patient interface layer 108. The adhesive deposits 128 on second side 120 of wicking layer 106 aid in adhering wound dressing 100 to an application site. The adhesive deposits 128 extend across the entire second side 120 of wicking layer 106 in an even pattern, as shown in FIG. 7, or may extend around the perimeter of second side 120 of wicking layer 106 such that the center 130 of second side 120 is free of adhesive, as shown in FIG. 8. The center 130 of second side 120 which is free of adhesives may be configured to contact the wound, such that the adhesive deposits 128 do not stick to or further damage the wound. Still other patterns and embodiments of adhesive deposits 128 are possible.

In some embodiments, wicking layer 106 is configured to aid in perspiration management within wound dressing 100. Wicking layer 106 draws wound exudate from the wound bed and perspiration from the skin surrounding the wound bed, and then laterally transfers the wound exudate and perspiration into absorbent layer 104. Wicking layer 106 may directly contact the wound bed and surrounding skin through perforations 126 within patient interface layer 108. In other embodiments, wicking layer 106 may comprise a plurality of fenestrations rather than perforations 126. It is to be understood that perforations 126 referred to herein may alternatively comprise fenestrations. In some embodiments, such as shown in FIGS. 3 and 6, perforations 126 extend across the entirety of patient interface layer 108. Thus, wicking layer 106 contacts both the wound bed and the surrounding skin through perforations 126, and draws both wound exudate from the wound bed and perspiration from the surrounding skin through the perforations and into wicking layer 107. In other embodiments, such as shown in FIGS. 4, 7, and 8, patient interface layer 108 has a central opening, such that wicking layer 106 is in direct contact with the wound bed through the central opening, and is in contact with the surrounding skin through perforations 126 around the perimeter of patient interface layer 108. When wicking layer 106 contacts the wound bed through the central opening, wicking layer 106 rapidly increases the uptake of wound exudate from the wound bed. Wicking layer 106 contacts the skin surrounding the wound bed through perforations 126 which may form the adhesive border of wound dressing 100.

Wicking layer 106 aids in drawing perspiration from underneath the adhesive border, through perforations 126 in patient interface layer 108, and into wicking layer 106. Once fluids, including wound exudate and perspiration, have entered into wicking layer 106, wicking layer 106 is configured to laterally transfer the fluids towards the absorbent layer 104, where they are further contained and evaporated through cover layer 102. Wicking layer 106 is intended to promote the transfer of fluids, both from the wound bed and from the surrounding skin, towards the absorbent layer 104.

Patient Interface Layer

In some embodiments, wound dressing 100 includes a patient interface layer 108. Patient interface layer 108 is shown to include a first side 122 and a second side 124 opposite first side 122. Second side 124 is configured to contact a wound bed. In some embodiments, patient interface layer 108 may lie entirely within the confines of a wound bed. In some embodiments, patient interface layer 108 may have a wound region, located centrally within wound dressing 100, the wound region configured to cover the wound bed. Patient interface layer 108 may further have a border region surrounding the centrally located wound region. The border region may be configured to overlie a periwound region that surrounds the wound bed. In some embodiments, patient interface layer 108 may comprise a silicone, hydrogel, polyurethane or similar material. In some embodiments, patient interface layer 108 may be configured to provide a low to moderate tack adhesive in order to anchor wound dressing 100 to the application site, e.g. a wound bed and the surrounding skin. In some embodiments, patient interface layer 108 may form a continual adhesive border surrounding the wound bed in order to ensure a perimeter seal once the wound dressing 100 is applied.

In some embodiments, a perimeter of first side 122 of patient interface layer 108 may be laminated or otherwise adhered to second side 112 of cover layer 102. Second side 112 of cover layer 102 may comprise a high tack adhesive in order to adhere to first side 122 of patient interface layer 108. The adhesive may solely be on the perimeter of second side 112, such that the cover layer 102 and patient interface layer 108 are adhered together to surround absorbent layer 104 and wicking layer 106. The adhesion of cover layer 102 to patient interface layer 108 further provides the adhesive border surrounding absorbent layer 104. In some embodiments, the perimeter of patient interface layer 108 is even with the perimeter of cover layer 102. In some embodiments, the perimeter of patient interface layer 108 extends beyond a perimeter of wicking layer 106 by a distance of between 2 mm and 10 mm.

In some embodiments, such as shown in FIGS. 3-4 and 6-8, patient interface layer 108 may comprise a plurality of perforations 126. Such perforations 126 may increase flexibility of wound dressing 100 and increase the uptake of wound exudate into through patient interface layer 108 and towards wicking layer 106. In some embodiments, perforations 126 may be evenly distributed on the entirety of patient interface layer 108, such as shown in FIGS. 3 and 6. In other embodiments, such as shown in FIGS. 4, 7, and 8, perforations 126 extend around only a border portion, e.g., forming a "picture frame" shape, around the edges of patient interface layer 108. In other embodiments, perforations 126 may form any pattern around the entirety of patient interface layer 108. In some embodiments, perforations 126 may extend through only a portion of patient interface layer 108. In other embodiments, perforations 126 may extend entirely from first side 122 to second side 124 of patient interface layer 108, such that they form small openings through the patient interface layer 108. Perforations 126 are intended to allow wicking layer 106 to directly contact the wound bed and/or surrounding skin through the patient interface layer 108, in order to promote the uptake of wound exudate and perspiration into wicking layer 106 and towards absorbent layer 108.

In some embodiments, such as the embodiment shown in FIGS. 3 and 5-6, patient interface layer 108 is a sheet-like layer, such that patient interface layer 108 extends across the entirety of wound dressing 100. While second side 124 of patient interface layer 108 contacts a wound bed, first side 122 of patient interface layer 108 contacts the second side 120 of wicking layer 106. In some embodiments, first side 122 of patient interface layer 108 is adhered to second side 120 of wicking layer 106. In some embodiments, adhesive deposits 128 on second side 120 of wicking layer 106 may adhere wicking layer 106 to first side 122 of patient interface layer 108. Perforations 126 within the patient interface layer 108 allow the wicking layer 106 to wick wound exudate from the wound bed and towards the absorbent layer 104 through the patient interface layer 108. A bottom perspective view of the patient interface layer 108 in its sheet-like form is shown in FIG. 6, according to an exemplary embodiment. Perforations 126 allow for rapid uptake of fluid by the wicking layer 106 through the patient interface layer 108.

In other embodiments, such as the embodiment shown in FIGS. 4 and 7-8, patient interface layer 108 is substantially ring-shaped or "picture-frame" shaped, such that there is a central opening. Thus, when wicking layer 106 is placed over patient interface layer 108, a central portion of a second side 120 of wicking layer 106 remains exposed to contact the wound bed. The wicking layer 106 may be placed over the ring-shaped patient interface layer 108, and may overlap the ring-shaped patient interface layer 108 on the edges. In some embodiments, adhesive deposits 128 on second side 120 of wicking layer 106 are exposed through the opening of patient interface layer 108, and may contact the application site. In some embodiments, the ring-shaped patient interface layer 108 may extend past the outer perimeter of wicking layer 106 by between 2 mm and 10 mm. In the embodiment shown in FIG. 7, the bottom of the ring-shaped patient interface layer 108 surrounds the wicking layer 106. Adhesive deposits 128 coat the entirety of second side 120 of wicking layer 106 that is exposed through the opening in ring-shaped patient interface layer 108. In the embodiment shown in FIG. 8, adhesive deposits 128 coat only a portion of the second side 120 of wicking layer, leaving the center 130 free of adhesive, for contacting the wound bed.

According to exemplary embodiments, wound dressing 100 has multiple advantages over previous wound dressings. Wound dressing 100 provides for superior perspiration management in comparison to traditional wound dressings. Wound dressing 100 allows for the rapid uptake of wound exudate and other fluids from a wound bed. The incorporation of wicking layer 106 into wound dressing 100 promotes fluid uptake and transfers fluid towards absorbent layer 104 and cover layer 102 where it may evaporate into the surrounding atmosphere. The layers and configurations of wound dressing 100 also eliminates the risk of the dressing lifting from the application site which is traditionally caused by moisture within a dressing. The layers of wound dressing 100 provide an adhesive border surrounding absorbent layer 104 in order to prevent fluid leakage from the wound dressing and further prevent the dressing from lifting off the application site. Wicking layer 106 wicks perspiration from underneath the adhesive border through perforations within the patient interface layer 108 in order to prevent the dressing 100 from lifting. This configuration aids in reducing the impact of the wound dressing 100 on the patient's skin, including the healthy skin surrounding the wound bed, as there is less risk of maceration and further damage to the patient.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A wound dressing comprising:
   a patient interface layer configured to engage a wound bed, and having a first side and a second side, the second side configured to face the wound bed, wherein the patient interface layer comprises a plurality of perforations;
   a wicking layer having a first side and a second side, the second side configured to face the first side of the patient interface layer;
   an absorbent layer having a first side and a second side, the second side configured to face the first side of the wicking layer; and
   a cover layer having a first side and a second side, the second side configured to face the first side of the absorbent layer,
   wherein a perimeter of the first side of the wicking layer is adhered to the second side of the cover layer, forming an adhesive border surrounding the wicking layer and the absorbent layer, wherein the wicking layer is configured to peripherally wick perspiration from underneath the adhesive border towards a center of the wicking layer and upwards towards the absorbent layer, and wherein the wicking layer is configured to contact the wound bed and surrounding skin through the perforations in the patient interface layer and to wick moisture from the wound bed and the surrounding skin through the perforations.

2. The wound dressing of claim 1, wherein the wicking layer is further configured to wick wound exudate from the wound bed, through the wicking layer, and upwards towards the absorbent layer and to increase an amount of evaporation of wound exudate from the wound dressing.

3. The wound dressing of claim 1, wherein the second side of the wicking layer comprises a plurality of adhesive deposits.

4. The wound dressing of claim 3, wherein the adhesive deposits coat the entirety of the second side of the wicking layer in a pattern.

5. The wound dressing of claim 3, wherein the adhesive deposits coat only a portion of the second side of the wicking layer in a pattern, leaving a central portion of the second side of the wicking layer free of the adhesive deposits.

6. The wound dressing of claim 1, wherein the second side of the cover layer is further adhered to the first side of the wicking layer around the perimeter, surrounding the absorbent layer such that the absorbent layer is free-floating between the wicking layer and the cover layer.

7. The wound dressing of claim 1, wherein a perimeter of the cover layer extends beyond the perimeter of the wicking layer by a distance of between 2 mm and 10 mm.

8. The wound dressing of claim 1, wherein the plurality of perforations are distributed around a perimeter of the patient interface layer.

9. The wound dressing of claim 1, wherein the patient interface layer comprises an adhesive-coated ring configured to peripherally surround and overlap the wicking layer, such that the wicking layer is configured to directly contact the wound bed and a portion of the surrounding skin through a central opening in the adhesive-coated ring.

10. The wound dressing of claim 1, wherein the patient interface layer comprises a silicone or hydrogel material.

11. The wound dressing of claim 1, wherein the cover layer comprises one of a polyurethane or polyethylene foam.

12. A method of making a wound dressing, comprising:
    providing a patient interface layer configured to engage a wound bed, and having a first side and a second side, the second side configured to face the wound bed, wherein a plurality of perforations are distributed around a perimeter of the patient interface layer;
    placing a wicking layer, having a first side and a second side, atop the patient interface layer;
    placing an absorbent layer, having a first side and a second side, atop the wicking layer; and
    adhering a cover layer, having a high moisture vapor transmission rate, to the patient interface layer and the wicking layer, such that the cover layer is atop the absorbent layer, forming an adhesive border surrounding the absorbent layer,
    wherein the wicking layer is configured to peripherally wick perspiration from underneath the adhesive border towards a center of the wicking layer and upwards towards the absorbent layer, and wherein the patient interface layer comprises an adhesive-coated ring configured to peripherally surround and overlap the wicking layer, such that the wicking layer is configured to directly contact the wound bed and surrounding skin through a central opening in the adhesive-coated ring.

13. The method of claim 12, further comprising providing a plurality of adhesive deposits on the second side of the wicking layer, such that the plurality of adhesive deposits are in contact with the wound bed and the surrounding skin through the central opening.

14. The method of claim 13, wherein a central portion of the second side of wicking layer is free of adhesive deposits.

15. The method of claim 12, wherein the cover layer extends beyond a perimeter of the wicking layer by a distance of between 2 mm and 10 mm.

16. A wound dressing comprising:
    a patient interface layer having a plurality of fenestrations or perforations, the patient interface layer having a wound region configured to cover a wound bed, and a border region configured to overlie a periwound region surrounding the wound bed, wherein the border region includes at least some of the plurality of fenestrations or perforations;
    a wicking layer atop the patient interface layer and substantially coextensive with the patient interface layer, wherein the wicking layer is configured to contact at least the periwound region through the fenestrations or perforations in the patient interface layer and to wick moisture therethrough;
    an absorbent layer atop the wicking layer, the absorbent layer having a perimeter that is inset from, and non-coextensive with, the border region of the patient interface layer, the absorbent layer configured to draw perspiration from the periwound region up through the fenestrations or perforations in the border region and laterally through the wicking layer to the absorbent layer, and to draw wound exudate from the wound bed up through the fenestrations or perforations in the wound region and directly up through the wicking layer to the absorbent layer; and
    a cover layer atop the absorbent layer, the cover layer having an underside with an adhesive provided at least partially thereon that bonds with at least one of the wicking layer and the patient interface layer.

* * * * *